United States Patent
Mastboim et al.

(10) Patent No.: US 11,921,119 B2
(45) Date of Patent: *Mar. 5, 2024

(54) METHODS OF PROGNOSIS AND TREATMENT

(71) Applicant: MeMed Diagnostics Ltd., Tirat HaCarmel (IL)

(72) Inventors: Niv Steven Mastboim, Haifa (IL); Tanya Michelle Gottlieb, Rehovot (IL); Kfir Oved, Hof HaCarmel (IL); Eran Eden, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 332 days.

This patent is subject to a terminal disclaimer.

(21) Appl. No.: 17/077,049

(22) Filed: Oct. 22, 2020

(65) Prior Publication Data
US 2021/0247405 A1  Aug. 12, 2021

Related U.S. Application Data

(60) Provisional application No. 62/972,134, filed on Feb. 10, 2020.

(51) Int. Cl.
*G01N 33/68* (2006.01)

(52) U.S. Cl.
CPC ... *G01N 33/6863* (2013.01); *G01N 2333/521* (2013.01); *G01N 2333/5412* (2013.01); *G01N 2333/585* (2013.01); *G01N 2333/70575* (2013.01)

(58) Field of Classification Search
None
See application file for complete search history.

(56) References Cited

FOREIGN PATENT DOCUMENTS

WO  WO-2018060998 A1 * 4/2018 ............. G01N 33/50

OTHER PUBLICATIONS

Waiker et al (J Am Soc Nephrol. Jan. 2012; 23(1): 13-21) (Year: 2012).*
Mayeux (NeuroRx. Apr. 2004;1(2):182-8) (Year: 2004).*

* cited by examiner

*Primary Examiner* — Brian Gangle
*Assistant Examiner* — Andrea K McCollum

(57) ABSTRACT

A method of determining a management course for treating a subject showing symptoms of a disease is disclosed. The method comprises measuring the TRAIL protein level in a blood sample of the subject, wherein when the TRAIL level is above a predetermined amount, the subject is treated as a low-risk patient.

15 Claims, 2 Drawing Sheets

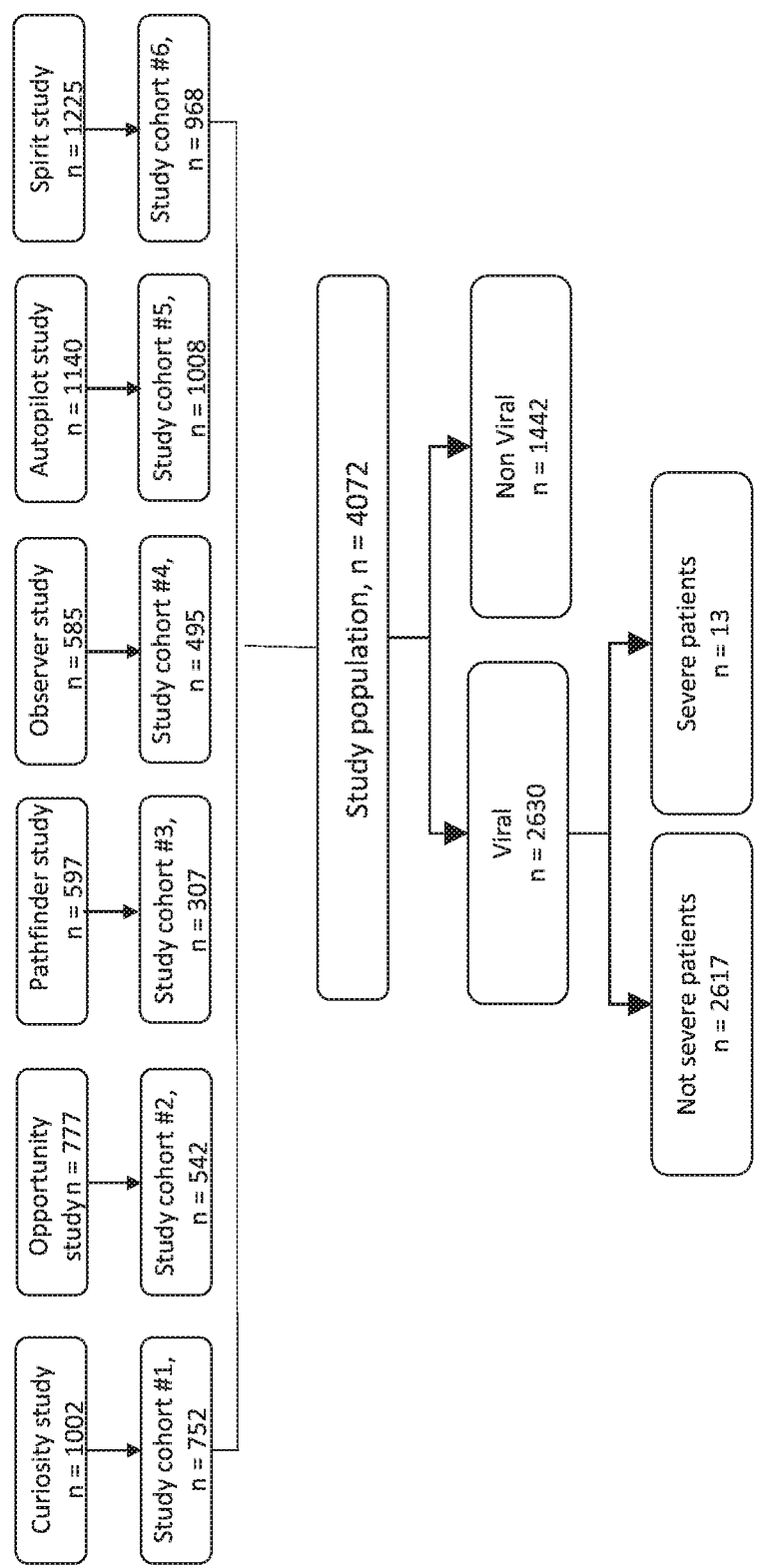

METHODS OF PROGNOSIS AND TREATMENT

RELATED APPLICATION(S)

Figure 1:
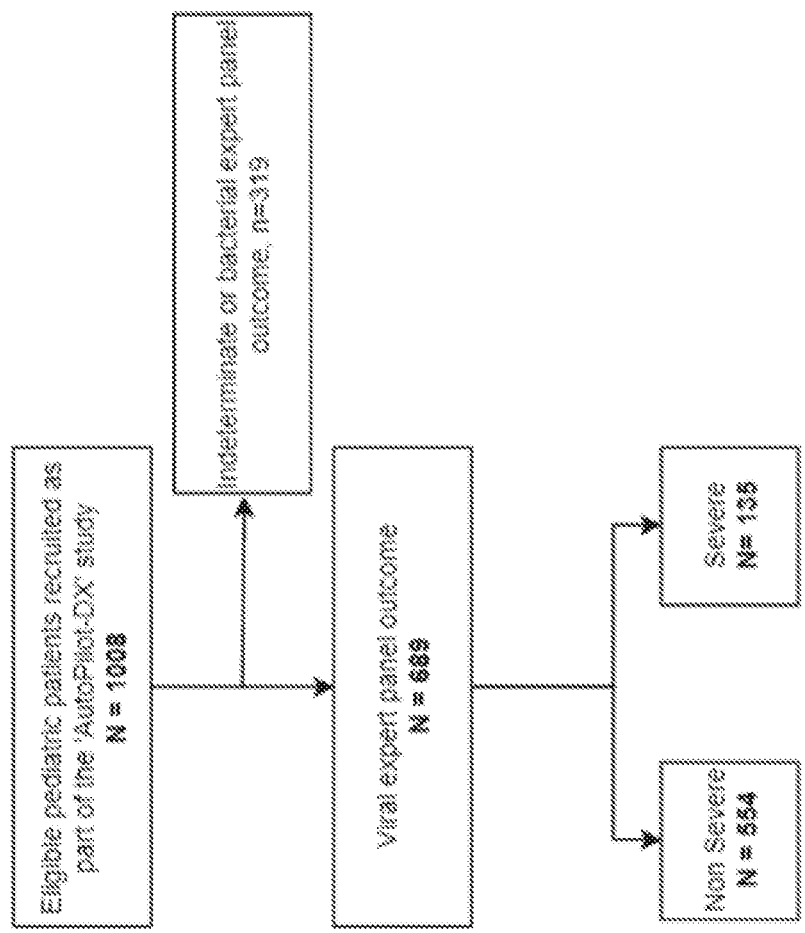

This application claims the benefit of priority under 35 USC § 119(e) of U.S. Provisional Patent Application No. 62/972,134 filed on Feb. 10, 2020, the contents of which are all incorporated by reference as if fully set forth herein in their entirety.

FIELD AND BACKGROUND OF THE INVENTION

The present invention, in some embodiments thereof, relates to methods and prognosis of disease and treatment thereof based on the protein TNF-related apoptosis-inducing ligand (TRAIL) levels.

Disease assessment is one of the most important tasks in management of infectious disease patients. Complement to determining infection etiology, predicting patient prognosis may affect various aspects of patient management including treatment, diagnostic tests (e.g., microbiology, blood chemistry, radiology etc.), and admission. Timely identification of patients with higher chance for poor prognosis may result in more aggressive patient management procedures including for example, intensive care unit (ICU) admission, advanced therapeutics, invasive diagnostics or surgical intervention, which could reduce complications and mortality.

WO 2013/117746 teaches biomarkers including TNF-related apoptosis-inducing ligand (TRAIL) for distinguishing between a bacterial and viral infection.

Additional background art includes WO 2016/024278, WO2018/060998 and WO2018/060999.

SUMMARY OF THE INVENTION

According to an aspect of some embodiments of the present invention there is provided a method of determining a management course for treating a subject who is pre-diagnosed as having a viral infection, comprising measuring the TNF-related apoptosis-inducing ligand (TRAIL) protein level in a blood sample of the subject, wherein when the TRAIL level is above a predetermined level, the subject is treated as a low-risk patient.

According to an aspect of some embodiments of the present invention there is provided a method of determining a management course for treating a subject who is pre-diagnosed as having a viral infection and is being treated as a high risk patient, comprising measuring the TRAIL protein level in a blood sample of the subject, wherein when the TRAIL level is above a predetermined level, the management of the subject is altered to one suitable for a low-risk patient.

According to some embodiments of the invention, the subject is being treated with a management selected from the group consisting of mechanical ventilation, invasive monitoring, last-resort drug, sedation, intensive care admission, surgical intervention and hospital admittance.

According to some embodiments of the invention, the management suitable for a low-risk patient is selected from the group consisting of cessation of mechanical ventilation, cessation of invasive monitoring, cessation of last-resort drug administration, cessation sedation, transfer out of intensive care and release from hospital.

According to some embodiments of the invention, the treatment of a low-risk patient comprises hospital release.

According to some embodiments of the invention, the blood sample is a fraction of whole blood.

According to some embodiments of the invention, the blood sample comprises cells selected from the group consisting of lymphocytes, monocytes and granulocytes.

According to some embodiments of the invention, fraction is serum or plasma.

According to some embodiments of the invention, the measuring is determined electrophoretically or immunochemically.

According to some embodiments of the invention, the immunochemical determination is effected by lateral flow immunoassay, flow cytometry, radioimmunoassay, immunofluorescence or by an enzyme-linked immunosorbent assay.

According to some embodiments of the invention, the subject is a child.

According to some embodiments of the invention, the viral disease is a coronavirus infection.

According to some embodiments of the invention, the predetermined level is above 145 pg/ml.

According to some embodiments of the invention, the predetermined level is above 120 pg/ml.

According to some embodiments of the invention, the method further comprises measuring the level of IP10.

According to some embodiments of the invention, the method further comprises measuring the level of at least one determinant set forth in Table 4.

According to some embodiments of the invention, the at least one determinant is selected from the group consisting of IP10, PCT, IL-6 and CRP.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1: Clinical study workflow.

FIG. 2: Clinical study workflow. Severe is defined as any one of the following: ICU admission, intubation or 28-day mortality.

DESCRIPTION OF SPECIFIC EMBODIMENTS OF THE INVENTION

The present invention, in some embodiments thereof, relates to methods and prognosis of viral disease and treatment thereof based on the level of protein TNF-related apoptosis-inducing ligand (TRAIL).

Disease assessment is one of the most important tasks in management of infectious disease patients. As a complement to determining infection etiology, predicting patient prognosis may affect various aspects of patient management including treatment, diagnostic tests (e.g., microbiology, blood chemistry, radiology etc.), and admission. Timely identification of patients with higher chance for poor prognosis may result in more aggressive patient management procedures including for example, ICU admission, advanced therapeutics, invasive diagnostics or surgical intervention, which could reduce complications and mortality. The present inventors previously discovered that TNF-related apoptosis-inducing ligand (TRAIL) levels are decreased in bacterial patients and increased in viral patients compared to non-infectious subjects. Based on their findings, they suggested TRAIL as a diagnostic marker for distinguishing between bacterial and viral patients (e.g. WO 2013/117746). In addition, the present inventors noted that very low TRAIL levels are correlated with different aspects of disease severity and thus could be used for tailoring the correct patient management course (e.g. WO2018/060998 and WO2018/060999).

The present inventors have now discovered a new threshold for TRAIL, which can distinguish between a virally infected subject of low risk and a virally infected subject of high risk.

Thus, according to the first aspect of the present invention there is provided a method of determining a management course for treating a subject who is pre-diagnosed as having a viral infection, comprising measuring the TNF-related apoptosis-inducing ligand (TRAIL) protein level in a blood sample of the subject, wherein when the TRAIL level is above a predetermined level, the subject is treated as a low-risk patient A "subject" in the context of the present invention may be a mammal (e.g. human, dog, cat, horse, cow, sheep, pig or goat). According to another embodiment, the subject is a bird (e.g. chicken, turkey, duck or goose). According to a particular embodiment, the subject is a human. The subject may be male or female. The subject may be an adult (e.g. older than 18, 21, or 22 years or a child (e.g. younger than 18, 21 or 22 years). In another embodiment, the subject is an adolescent (between 12 and 21 years), an infant (29 days to less than 2 years of age) or a neonate (birth through the first 28 days of life).

The subjects of this aspect of the present invention typically present with symptoms of the viral disease.

Exemplary symptoms of viral diseases include but are not limited to abnormal blood pressure, abnormal heart rate, abnormal red blood count, abnormal white blood count, abnormal body temperature, abnormal respiratory rate, abnormal lucidity or alertness.

Additional symptoms include but are not limited to fever, nausea, headache, sore throat, runny nose, rash and/or muscle soreness.

Exemplar viruses that cause diseases in humans include those set forth in Table 1 herein below.

TABLE 1

| Family | Baltimore group | Important species | envelopment |
| --- | --- | --- | --- |
| Adenoviridae | Group I (dsDNA) | Adenovirus | non-enveloped |
| Herpesviridae | Group I (dsDNA) | Herpes simplex, type 1, Herpes simplex, type 2, Varicella-zoster virus, Epstein-Barr virus, Human cytomegalovirus, Human herpesvirus, type 8 | enveloped |
| Papillomaviridae | Group I (dsDNA) | Human papillomavirus | non-enveloped |
| Polyomaviridae | Group I (dsDNA) | BK virus, JC virus | non-enveloped |
| Poxviridae | Group I (dsDNA) | Smallpox | enveloped |
| Hepadnaviridae | Group VII (dsDNA-RT) | Hepatitis B virus | enveloped |
| Family | Baltimore group | Important species | envelopment |
| Parvoviridae | Group II (ssDNA) | Parvovirus B19 | non-enveloped |
| Astroviridae | Group IV (positive-sense ssRNA) | Human astrovirus | non-enveloped |
| Caliciviridae | Group IV (positive-sense SSRNA) | Norwalk virus | non-enveloped |
| Picornaviridae | Group IV (positive-sense ssRNA) | coxsackievirus, hepatitis A virus, poliovirus, rhinovirus | non-enveloped |
| Coronaviridae | Group IV (positive-sense SSRNA) | Severe acute respiratory syndrome virus | enveloped |
| Flaviviridae | Group IV (positive-sense ssRNA) | Hepatitis C virus, yellow fever virus, dengue virus, West Nile virus, TBE virus | enveloped |
| Togaviridae | Group IV (positive-sense ssRNA) | Rubella virus | enveloped |
| Hepeviridae | Group IV (positive-sense SSRNA) | Hepatitis E virus | non-enveloped |
| Retroviridae | Group VI (ssRNA-RT) | Human immunodeficiency virus (HIV) | enveloped |
| Orthomyxoviridae | Group V (negative-sense ssRNA) | Influenza virus | enveloped |
| Family | Baltimore group | Important species | envelopment |
| Arenaviridae | Group V (negative-sense ssRNA) | Lassa virus | enveloped |
| Bunyaviridae | Group V (negative-sense ssRNA) | Crimean-Congo hemorrhagic fever virus, Hantaan virus | enveloped |
| Filoviridae | Group V (negative-sense SSRNA) | Ebola virus, Marburg virus | enveloped |
| Paramyxoviridae | Group V (negative-sense ssRNA) | Measles virus, Mumps virus, Parainfluenza virus, Respiratory syncytial virus, | enveloped |

TABLE 1-continued

| Family | Baltimore group | Important species | envelopment |
|---|---|---|---|
| Rhabdoviridae | Group V (negative-sense ssRNA) | Rabies virus | enveloped |
| Unassigned | Group V (negative-sense ssRNA) | Hepatitis D | enveloped |
| Reoviridae | Group III (dsRNA) | Rotavirus, Orbivirus, Coltivirus, Banna virus | non-enveloped |

Additional contemplated viruses include, but are not limited to human metapneumovirus, bocavirus and enterovirus.

According to a particular embodiment, the virus is a respiratory virus, including, but not limited to influenza, RSV and Coronavirus.

Examples of coronaviruses include: human coronavirus 229E, human coronavirus OC43, SARS-CoV, HCoV NL63, HKU1, MERS-CoV and SARS-CoV-2.

According to a specific embodiment, the virus is SARS-CoV-2.

According to another specific embodiment, the virus is RSV, Flu A, Flu B, HCoV or SARS-Cov-2.

Exemplary viral diseases include, but are not limited to those set forth in Table 2.

TABLE 2

| Diseases |
|---|
| gastroenteritis |
| keratoconjunctivitis |
| pharyngitis |
| croup |
| pharyngoconjunctival fever |
| pneumonia |
| cystitis |
| Hand, foot and mouth disease |
| pleurodynia |
| aseptic meningitis |
| pericarditis |
| myocarditis |
| infectious mononucleosis |
| Burkitt's lymphoma |
| Hodgkin's lymphoma |
| nasopharyngeal carcinoma |
| acute hepatitis |
| chronic hepatitis |
| hepatic cirrhosis |
| hepatocellular carcinoma |
| herpes labialis, cold sores - can recur by latency |
| gingivostomatitis in children |
| tonsillitis & pharyngitis in adults |
| keratoconjunctivitis |
| Aseptic meningitis |
| infectious mononucleosis |
| Cytomegalic inclusion disease |
| Kaposi sarcoma |
| multicentric Castleman disease |
| primary effusion lymphoma |
| AIDS |
| influenza |
| (Reye syndrome) |
| measles |
| postinfectious encephalomyelitis |
| mumps |
| hyperplastic epithelial lesions (common, flat, plantar and anogenital warts, laryngeal papillomas, epidermodysplasia verruciformis |

TABLE 2-continued

| Diseases |
|---|
| Malignancies for some species (cervical carcinoma, squamous cell carcinomas) |
| croup |
| pneumonia |
| bronchiolitis |
| common cold |
| poliomyelitis |
| rabies (fatal encephalitis) |
| congenital rubella |
| German measles |
| chickenpox |
| herpes zoster |
| Congenital varicella syndrome |

According to a specific embodiment, the viral disease is COVID-19.

Methods of pre-diagnosing viral diseases include for example by clinical assessment, PCR analysis, sequencing analysis, viral culture, antibody or antigen testing, or by use of host immune response measurements.

Thus, in one embodiment, the subject of this aspect of the present invention is one who is positive for a viral disease (e.g. COVID-19) as corroborated by a standard PCR test.

For any of the aspects disclosed herein, the term "measuring" or "measurement," or alternatively "detecting" or "detection," means assessing the presence, absence, quantity or amount (which can be an effective amount) of the determinant within a clinical or subject-derived sample, including the derivation of qualitative or quantitative concentration levels of such determinants.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, interstitial fluid, amniotic fluid, sample collected by a nasal swab or whole blood cells.

In a particular embodiment, the sample is a blood sample—e.g. serum, plasma, whole blood. The sample may be a venous sample, peripheral blood mononuclear cell sample or a peripheral blood sample. Preferably, the sample comprises white blood cells including for example granulocytes, lymphocytes and/or monocytes. In one embodiment, the sample is depleted of red blood cells.

The sample is preferably derived from the subject no more than 72 hours, no more than 60 hours, no more than 48 hours, no more than 36 hours, no more than one 24 hours or even no more than 12 hours following symptom onset.

The sample may be fresh or frozen.

According to a particular embodiment, the subject does not show signs of having had a heart attack (e.g. has a normal level of creatine kinase, troponin or serum myoglobin, and/or has a normal ECG or EKG).

According to yet another embodiment, the subject does not have cancer.

TRAIL: The protein encoded by this gene is a cytokine that belongs to the tumor necrosis factor (TNF) ligand family. The present invention contemplates measuring either the soluble and/or the membrane form of this protein. In one embodiment, only the soluble form of this protein is measured. Additional names of the gene include without limitations APO2L, TNF-related apoptosis-inducing ligand, TNFSF10 and CD253. This protein binds to several members of the TNF receptor superfamily such as TNFRSF10A/

TRAILR1, TNFRSF10B/TRAILR2, TNFRSF10C/TRAILR3, TNFRSF10D/TRAILR4, and possibly also to TNFRSF11B/OPG.

Additional information concerning TRAIL is provided in Table 3, herein below.

TABLE 3

| Protein symbol | Full Gene Name | RefSeq DNA sequence | RefSeq proteins |
|---|---|---|---|
| TRAIL | Tumor necrosis factor superfamily member 10 | NC_000003.12<br>NC_018914.2<br>NT_005612.17 | NP_001177871.1<br>NP_001177872.1<br>NP_003801.1 |

Methods of measuring the level of TRAIL polypeptide are well known in the art and include, e.g., immunoassays based on antibodies to proteins, aptamers or molecular imprints.

TRAIL can be detected in any suitable manner, but are typically detected by contacting a sample from the subject with an antibody, which binds the TRAIL and then detecting the presence or absence of a reaction product. The antibody may be monoclonal, polyclonal, chimeric, or a fragment of the foregoing, and the step of detecting the reaction product may be carried out with any suitable immunoassay.

In one embodiment, the antibody which specifically binds the determinant is attached (either directly or indirectly) to a signal producing label, including but not limited to a radioactive label, an enzymatic label, a hapten, a reporter dye or a fluorescent label.

Immunoassays carried out in accordance with some embodiments of the present invention may be homogeneous assays or heterogeneous assays. In a homogeneous assay the immunological reaction usually involves the specific antibody (e.g., anti-determinant antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label". The determinant can also be detected with antibodies using flow cytometry. Those skilled in the art will be familiar with flow cytometric techniques which may be useful in carrying out the methods disclosed herein (Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein, rhodamine) in accordance with known techniques.

In particular embodiments, the antibodies of the present invention are monoclonal antibodies.

Suitable sources for antibodies for the detection of determinants include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide determinants described herein.

The presence of a label can be detected by inspection, or a detector which monitors a particular probe or probe combination is used to detect the detection reagent label.

Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook [The Immunoassay Handbook. Third Edition. 2005].

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Soluble TRAIL and membrane TRAIL can be distinguished by using different measuring techniques and samples. For example, Soluble TRAL can be measured without limitation in cell free samples such as serum or plasma, using without limitation lateral flow immunoassay (LFIA), as further described herein below. Membrane TRAIL can be measured in samples that contain cells using cell based assays including without limitation flow cytometry, ELISA, and other immunoassays.

Lateral Flow Immunoassays (LFIA): This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Different formats may be adopted in LFIA. Strips used for LFIA contain four main components. A brief description of each is given before describing format types.

Sample application pad: It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate pad: It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose membrane: It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent pad: It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich format: In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive format: Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex detection format: Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are interdependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels: Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold nanoparticles: Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic particles and aggregates: Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and luminescent materials: Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes: Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal carbon: Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection systems: In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares. Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated seruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

As mentioned above, when the TRAIL protein level in the sample (e.g. in the serum) is above a predetermined level, the subject is classified as a low-risk patient. The predetermined level may be above 120 pg/ml, above 125 pg/ml, above 130 pg/ml, above 135 pg/ml, above 140 pg/ml; above 145 pg/ml, above 150 pg/ml, above 155 pg/ml or even above 160 pg/ml.

In another embodiment, the predetermined level is above 100 pg/ml, 105 pg/ml, 110 pg/ml or 115 pg/ml.

The term "risk assessment" refers to as assignment of a probability to experience certain adverse events (e.g. death, hospitalization or admission to ICU) to an individual. Hereby, the individual may preferably be accounted to a certain risk category, wherein categories comprise for instance high risk versus low risk, or risk categories based on numeral values, such as risk category 1, 2, 3, etc. 2.

In one embodiment, the risk assessment is made in the emergency department of a hospital.

Emergency departments (ED) are progressively overwhelmed by patients with both urgent and non-urgent problems. This leads to overfilled ED waiting rooms with long waiting times, detrimental outcomes and unsatisfied patients. As a result, patients needing urgent care may not be treated in time, whereas patients with non-urgent problems may unnecessarily receive expensive and dispensable treatments. Time to effective treatment is among the key predictors for outcomes across different medical conditions, including patients with septicemia, pneumonia, stroke and myocardial infarction. For these reasons, the present inventors propose use of the presently disclosed risk stratification system in the ED is essential for an optimal initial triage of medical patients.

In another embodiment, the risk assessment is made in the intensive care unit of a hospital.

The risk measurement may be used to determine a management course for the patient. The risk measurement may aid in selection of treatment priority and also site-of-care decisions (i.e. outpatient vs. inpatient management) and early identification and organization of post-acute care needs.

When a patient has been assessed as being at high risk, the management course is typically more aggressive than if he had not been assessed as being at high risk. Thus, treatment options such as mechanical ventilation, life support, catheterization, hemofiltration, invasive monitoring, sedation, intensive care admission, surgical intervention, drug of last resort, anti-viral drug, immunomodulator treatment and hospital admittance may be selected which may otherwise not have been considered the preferred method of treatment if the patient had not been assessed as being at high risk.

In one embodiment, when the TRAIL level of the viral patient is above 120 pg/ml, at least one of the following clinical decisions may be taken: no need for anti-viral treatment, no need for immunomodulatory treatment, discharge from hospital and/or no additional diagnostics required. When the TRAIL level of the viral patient is below 120 pg/ml, at least one of the following clinical decisions may be taken: start anti-viral treatment, consider immunomodulatory treatment, admit to ICU, perform viral PCR testing and/or perform imaging testing.

In one embodiment, when the TRAIL level of the viral patient is above 145 pg/ml, at least one of the following clinical decisions may be taken: no need for anti-viral treatment, no need for immunomodulatory treatment, discharge from hospital and/or no additional diagnostics required. When the TRAIL level of the viral patient is below 145 pg/ml, at least one of the following clinical decisions may be taken: start anti-viral treatment, consider immunomodulatory treatment, admit to ICU, perform viral PCR testing and/or perform imaging testing.

Classification of a subject into a low risk group according to these aspects of the present invention is preferably done with an acceptable level of clinical or diagnostic accuracy. An "acceptable degree of diagnostic accuracy", is herein defined as a test or assay (such as the test used in some aspects of the invention) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict risk with at least 75% total accuracy, more preferably 80%, 85%, 90%, 95%, 97%, 98%, 99% or greater total accuracy. Alternatively, the methods predict the correct management or treatment with an MCC larger than 0.2, 0.3, 0.4, 0.5, 0.6, 0.7, 0.8, 0.9 or 1.0.

On the basis of the level of TRAIL, the practitioner may determine a less severe treatment course than for a subject who represents with the same symptoms yet has a TRAIL protein serum level below the predetermined level (e.g. 145 pg/ml).

Thus, for example when the TRAIL level is below the predetermined amount, the practitioner may predict or recommend intensive care unit (ICU) admission.

According to another embodiment of the present invention, the TRAIL is used for predicting a prolonged hospital length of stay, or recommending an extended treatment and observation period.

In one embodiment, the subject is pre-diagnosed with viral infection and has been classified as a high risk. The subject is therefore under a management course for high risk patients. Upon further monitoring, it may be observed that the TRAIL level is above the predetermined level (e.g. 145 pg/ml) and therefore the management of the subject is changed e.g. cessation of invasive monitoring, cessation of mechanical ventilation, cessation of administration of immunomodulatory treatment, last-resort drug or anti-viral drug administration, lowering of dose of a drug, cessation of sedation, removal from ICU and put in a different ward.

Last resort drugs may be for example experimental agents that have not been given full FDA approval. Other last resort agents are those that are known to be associated with severe side effects. Another exemplary last resort agent is an experimental antiviral drug. Another exemplary last resort agent is a broad-spectrum antibiotic. Another exemplary last resort agent are drugs that have been approved for different indications.

It will be appreciated that agents that are not typically considered as last resort agents can also be provided, but in doses which exceed the clinically acceptable dose.

It will be appreciated that the TRAIL level may be used in conjunction with other markers/tests etc. in order to determine a management course and/or to assess risk to subject.

Exemplary markers include for example those disclosed in Table 4 herein below.

TABLE 4

| Protein symbol | Full Gene Name | RefSeq DNA sequence | RefSeq proteins |
|---|---|---|---|
| CRP | C-reactive protein, pentraxin-related | NC_000001.11<br>NT_004487.20<br>NC_018912.2 | NP_000558.2 |
| IP-10 | Chemokine (C-X-C motif) ligand 10 | NC_000004.12<br>NC_018915.2<br>NT_016354.20 | NP_001556.2 |

TABLE 4-continued

| Protein symbol | Full Gene Name | RefSeq DNA sequence | RefSeq proteins |
|---|---|---|---|
| IL1R/ ILIR1/ ILIRA | Interleukin 1 receptor, type I | NC_000002.12<br>NT_005403.18<br>NC_018913.2 | NP_000868.1<br>NP_001275635.1 |
| SAA/SAA1 | Serum amyloid A1 | NC_000011.10<br>NC_018922.2<br>NT_009237.19 | NP_000322.2<br>NP_001171477.1<br>NP_954630.1 |
| TREM1 | Triggering receptor expressed on myeloid cells 1 | NC_000006.12<br>NT_007592.16<br>NC_018917.2 | NP_001229518.1<br>NP_001229519.1<br>NP_061113.1 |
| TREM2 | Triggering receptor expressed on myeloid cells 2 | NC_000006.12<br>NT_007592.16<br>NC_018917.2 | NP_001258750.1<br>NP_061838.1 |
| RSAD2 | Radical S-adenosyl methionine domain containing 2 | NC_000002.12<br>NT_005334.17<br>NC_018913.2 | NP_542388.2 |
| NGAL | Lipocalin 2 | NC_000009.12<br>NC_018920.2<br>NT_008470.20 | NP_005555.2 |
| MMP8 | Matrix metallopeptidase 8 | NC_000011.10<br>NT_033899.9<br>NC_018922.2 | NP_001291370.1<br>NP_001291371.1<br>NP_002415.1 |
| MX1 | MX Dynamin-Like GTPase 1 | NC_000021.9<br>NT_011512.12<br>NC_018932.2 | NP_001138397.1<br>NP_001171517.1<br>NP_001269849.1<br>NP_002453.2 |
| Procalcitonin (PCT) | Calcitonin-related polypeptide alpha | NC_000011.10<br>NC_018922.2<br>NT_009237.19 | NP_001029124.1<br>NP_001029125.1<br>NP_001732.1 |
| IL-6 | Interleukin 6 | NC_000007.14<br>NT_007819.18<br>NC_018918.2 | NP_000591.1 |
| Neopterin | 2-amino-6-(1,2,3-trihydroxypropyl)-1H-pteridin-4-one IUPAC name | N/A | N/A |
| IL-2 | Interleukin 2 | NC_000004.12 | NP_000577.2<br>XP_016863666.1 |
| IL-7 | Interleukin 7 | NC_000008.11 | NP_000871.1<br>XP_011515824.1<br>XP_016868886.1<br>XP_011515825.1<br>NP_001186817.1<br>NP_001186815.1<br>NP_001186816.1 |
| IL-10 | Interleukin 10 | NC_000001.11 | NP_000563.1 |
| G-CSF/CSF3 | Colony Stimulating Factor 3 | NC_000017.11 | NP_000750.1<br>NP_001171618.1<br>NP_757373.1<br>NP_757374.2 |
| MIP-1a/CCL3 | C-C Motif Chemokine Ligand 3 | NC_000017.11<br>NT_187614.1<br>NT_187661.1 | NP_002974.1 |
| TNF-α | Tumor Necrosis Factor/Tumor Necrosis Factor-Alpha | NC_000006.12<br>NT_113891.3<br>NT_167244.2<br>NT_167245.2<br>NT_167246.2<br>NT_167247.2<br>NT_167248.2<br>NT_167249.2 | NP_000585.2 |

Furthermore, traditional risk factors and additional clinical parameters may be used to classify the severity of the disease.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

Exemplary combinations of markers which may be used for the risk management disclosed herein include, but are not limited to:
TRAIL+CRP; TRAIL+PCT; TRAIL+IL-6; TRAIL+IP-10; TRAIL+NGAL; TRAIL+IL-2; TRAIL+IL-7; TRAIL+IL-10; TRAIL+G-CSF; TRAIL+MIP-1a; TRAIL+TNF-α; TRAIL+CRP+PCT; TRAIL+CRP+NGAL; TRAIL+CRP+IP-10; TRAIL+CRP+IL-6; TRAIL+PCT+IL-6; TRAIL+PCT+IP-10; TRAIL+PCT+NGAL; TRAIL+CRP+IL-6+PCT; TRAIL+CRP+IL-6+NGAL; TRAIL+CRP+IL-6+IP-10; TRAIL+NGAL+IL-6+PCT; TRAIL+IP-10+IL-6+PCT; TRAIL+WBC; TRAIL+ANC; TRAIL+temperature; TRAIL+mean arterial pressure; TRAIL+pH arterial; TRAIL+heart rate; TRAIL+respiratory rate; TRAIL+AaDO2 or PaO2; TRAIL+sodium; TRAIL+potassium; TRAIL+creatinine; TRAIL+hematocrit.

Combining the levels of TRAIL and the other marker is typically affected using algorithms or formulas as described herein below.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations.

Of particular use in combining determinants are linear and non-linear equations and statistical classification analyses to determine the relationship between levels of determinants detected in a subject sample and the subject's risk assessment. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV).

Any formula may be used to combine TRAIL levels with the additional determinant into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formulas are described here, several other models and formula types beyond those mentioned herein and in the definitions above are well known to one skilled in the art. The actual model type or formula used may itself be selected from the field of potential models based on the performance and diagnostic accuracy characteristics of its results in a training population.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as age, time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

Some determinants may exhibit trends that depends on the patient age (e.g. the population baseline may rise or fall as a function of age). One can use an 'Age dependent normalization or stratification' scheme to adjust for age related differences. Performing age dependent normalization or stratification can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In the context of the present invention, the following abbreviations may be used: ANC=Absolute neutrophil count; ANN=Artificial neural networks; AUC=Area under the receiver operating curve; BP=*Bordetella pertussis*; CHF=Congestive heart failure; CI=Confidence interval; CID=Congenital immune deficiency; CLL=Chronic lymphocytic leukemia; CMV=Cytomegalovirus; CNS=Central nervous system; COPD=Chronic obstructive pulmonary disease; CP=*Chlamydophila* pneumonia; CRP=C-reactive protein; CSF=Cerebrospinal fluid; CV=Coefficient of variation; DOR=Diagnostic odds ratio; EBV=Epstein bar virus; eCRF=Electronic case report form; ED=Emergency department; ELISA=Enzyme-linked immunosorbent assay; FDR=False discovery rate; FMF=Familial Mediterranean fever; G-CSF=Granulocyte colony-stimulating factor; GM-CSF=Granulocyte-macrophage colony-stimulating factor; HBV=Hepatitis B virus; HCV=Hepatitis C virus; HI=*Haemophilus* influenza; HIV=Human immunodeficiency virus; IDE=Infectious disease experts; IL=Interleukin; IRB=institutional review board; IVIG=Intravenous immunoglobulin; KNN=K-nearest neighbors; LP=*Legionella pneumophila*; LR+=Positive likelihood ratio; LR−=Negative likelihood ratio; LRTI=Lower respiratory tract infections; mAb=Monoclonal antibodies; MDD=Minimum detectable dose; MDS=Myelodysplastic syndrome; MP=*Mycoplasma* pneumonia; MPD=Myeloproliferative disease; NPV=Negative predictive value; PCT=Procalcitonin; PED=Pediatric emergency department; PPV=Positive predictive value; QA=Quality assurance; RSV=Respiratory syncytial virus; RV=Rhinovirus; SIRS=systemic inflammatory syndrome; SP=*Streptococcus pneumonia*; STARD=Standards for Reporting of Diagnostic Accuracy; SVM=Support vector machine; TNF=Tumor necrosis factor; URTI=Upper respiratory tract infection; UTI=Urinary tract infection; WBC=White blood cell; WS=Wilcoxon rank-sum.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathews Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Mathews correlation coefficient (MCC), or as a likelihood, odds ratio, Receiver Operating Characteristic (ROC) curve, Area Under the Curve (AUC) among other measures.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The term "determinant" as used herein refers to a disease associated parameter or biomarker.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y.

(1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Methods

In the presented cohort, a total of 689 patients were defined as viral patients, of them 554 and 135 as non-severe and severe viral infections (FIG. 1), respectively. Patients with severe viral infection exhibited significantly lower TRAIL and IP-10 levels as compared to non-severe viral infections (TRAIL: non-severe 151±109; severe 117±87; P<0.001, IP-10: non-severe 639±525; severe 528±439; P=0.012, Table 5).

TABLE 5

Serum TRAIL and IP-10 levels in severe vs non severe viral infected patients * Severity defined as: hospitalization duration ≥5 days

|  | Non severe N Mean Median | Severe N Mean Median | P value |
| --- | --- | --- | --- |
| TRAIL | 554 151 114 | 135 117 91 | P < 0.001 |
| IP-10 | 554 639 (525) 477 | 135 528 390 | P = 0.012 |

TRAIL biomarker levels of 145 pg/ml were able to differentiate severe from non-severe viral infections. Hospitalized patients with TRAIL levels above 145 pg/ml had significantly lower hospitalization duration, required oxygen for less days, and were significantly less likely to be prescribed unnecessary antibiotics (Table 6).

TABLE 6

Hospitalization duration, lowest oxygen levels, oxygen days, and antibiotic prescription in hospitalized viral infected patients with different TRAIL levels.

|  | >145 pg/ml Mean (SD) Median | <=145 pg/ml Mean (SD) Median | P value |
| --- | --- | --- | --- |
| Hospitalization duration | 3.4 (2.1) 3.0 | 4.01 (2.6) 3.5 | 0.006 |
| Lowest oxygen levels | 0.96 (0.04) 0.97 | 0.95 (0.05) 0.96 | 0.005 |
| Oxygen days | 0.5 (1.4) 0.2 | 1.5 (2.5) 0.6 | 0.000 |
| Antibiotic prescription (%, n) | 24.0% (40/167) | 38/% (114/301) | 0.002 |

Example 2

Methods

In the presented cohort, patients meeting at least one of the following endpoints were defined as severe: ICU admission, need for mechanical ventilation and/or 28-days mortality.

A total of 2630 patients were defined as viral patients, of them 2617 and 13 as non-severe and severe viral infections according to the upper mentioned criteria (FIG. 2).

By dividing viral patients according to a specific TRAIL level, a distinct group of patients could be identified: patients at low risk for severe infection exhibited TRAIL levels above or equal to 120 pg/ml, (Table 7).

TABLE 7 risk group characterization, antibiotic prescription rates, and severe outcome likelihood ratios in patients with viral infections according to TRAIL levels.

| Risk group | TRAIL >=120 pg/ml Low | TRAIL <120 pg/ml High |
| --- | --- | --- |
| Antibiotic prescription (%, n) | 46% (545/1181) | 55% (802/1448) |
| Severe Outcome (%, n) | 0.2% (2/1181) | 0.8% (11/1448) |
| Likelihood Ratio (for meeting severe outcome) | 0.3 (0.1-1.3) | 1.5 (1.0-2.4) |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of determining a management course for a subject who has a diagnosis as having a severe coronaviral infection, comprising:
   (a) measuring the tumor necrosis factor-related apoptosis-inducing ligand (TRAIL) protein level in a blood sample of the subject, wherein when the TRAIL level is above 145 pg/ml, the method further comprises:
   (b) carrying out a management course selected from the group consisting of: (i) cessation of mechanical ventilation, (ii) cessation of invasive monitoring, (iii) cessation of last-resort drug administration, (iv) cessation of sedation, (v) transfer out of intensive care; and (vi) release from hospital.

2. The method of claim 1, wherein the management course comprises hospital release.

3. The method of claim 1, wherein said blood sample is a fraction of whole blood.

4. The method of claim 1, wherein said blood sample comprises cells selected from the group consisting of lymphocytes, monocytes and granulocytes.

5. The method of claim 3, wherein said fraction is serum or plasma.

6. The method of claim 1, wherein said measuring is determined electrophoretically or immunochemically.

7. The method of claim 6, wherein said immunochemical determination is effected by lateral flow immunoassay, flow cytometry, radioimmunoassay, immunofluorescence or by an enzyme-linked immunosorbent assay.

8. The method of claim 1, wherein the subject is a child.

9. The method of claim 1, further comprising measuring the level of Interferon gamma-induced protein 10 (IP10).

10. The method of claim 1, further comprising measuring the level of at least one determinant selected from the group consisting of: C-reactive protein (CRP), procalcitonin (PCT), IP10, Interleukin 1 receptor type I, Serum amyloid A1, Triggering receptor expressed on myeloid cells 1, Triggering receptor expressed on myeloid cells 2, Radical S-adenosyl methionine domain containing 2, Lipocalin 2, Matrix metallopeptidase 8, MX Dynamin-Like GTPase 1, Calcitonin-related polypeptide alpha, Interleukin 6, 2-amino-6-(1,2,3-trihydroxypropyl)-1H-pteridin-4-one, Interleukin 2, Interleukin 7, and Interleukin 10.

11. The method of claim 10, wherein said at least one determinant is selected from the group consisting of IP10, procalcitonin (PCT), Interleukin-6 (IL-6) and C-reactive protein (CRP).

12. A method of determining a management course for a subject having a coronaviral infection, comprising:
    (a) measuring TRAIL protein level in a blood sample of the subject, wherein when the TRAIL level is below 145 pg/ml, the method further comprises:
    (b) carrying out a management course selected from the group consisting of anti-viral treatment, immunomodulatory treatment, mechanical ventilation, invasive monitoring, last-resort drug administration, sedation, intensive care admission, surgical intervention and hospital admittance.

13. The method of claim 12, further comprising measuring the level of Interferon gamma-induced protein 10 (IP10).

14. The method of claim 12, further comprising measuring the level of at least one determinant selected from the group consisting of C-reactive protein (CRP), IP10, procalcitonin (PCT), Interleukin 1 receptor type 1, Serum amyloid A1, Triggering receptor expressed on myeloid cells 1, Triggering receptor expressed on myeloid cells 2, Radical S-adenosyl methionine domain containing 2, Lipocalin 2, Matrix metallopeptidase 8, MX Dynamin-Like GTPase 1, Calcitonin-related polypeptide alpha, Interleukin 6, 2-amino-6-(1,2,3-trihydroxypropyl)-1H-pteridin-4-one, Interleukin 2, Interleukin 7, and Interleukin 10.

15. The method of claim 14, wherein said at least one determinant is selected from the group consisting of IP10, procalcitonin (PCT), Interleukin-6 (IL-6) and C-reactive protein (CRP).

* * * * *